(12) United States Patent
Worcel

(10) Patent No.: US 9,375,242 B2
(45) Date of Patent: Jun. 28, 2016

(54) OSTEOSYNTHESIS DEVICE WITH PLATE AND PINS

(75) Inventor: Alexandre Worcel, Montlignon (FR)

(73) Assignees: Alexandre Worcel, Montlignon (FR); Manuel Worcel, Paris (FR); Julia Worcel, Montlignon (FR); Marie Worcel, Montlignon (FR); Albert Paoli, Pontoise (FR); Myriam Paoli, Pontoise (FR); Edouard Paoli, Pontoise (FR); Jean Paoli, Pontoise (FR); Bernard Lombardo-Fiault, Paris (FR); Alain Laumonier, Nesles la Vallée (FR); Rémi Laumonier, Pontoise (FR); Bruno Laumonier, Nesles la Vallée (FR); Yves Laumonier, Nesles la Vallée (FR); Nicolas Laumonier, Pontoise (FR); Ateliers Laumonier, Nesles la Vallée (FR)

( * ) Notice: Subject to any disclaimer, the term of this patent is extended or adjusted under 35 U.S.C. 154(b) by 112 days.

(21) Appl. No.: 14/114,995

(22) PCT Filed: May 21, 2012

(86) PCT No.: PCT/FR2012/051125
§ 371 (c)(1),
(2), (4) Date: Jan. 14, 2014

(87) PCT Pub. No.: WO2012/168613
PCT Pub. Date: Dec. 13, 2012

(65) Prior Publication Data
US 2014/0121711 A1    May 1, 2014

(30) Foreign Application Priority Data

Jun. 6, 2011 (FR) ...................................... 11 54878

(51) Int. Cl.
*A61B 17/80* (2006.01)

(52) U.S. Cl.
CPC ......... *A61B 17/8033* (2013.01); *A61B 17/8047* (2013.01)

(58) Field of Classification Search
CPC ........................ A61B 17/8033; A61B 17/8047
See application file for complete search history.

(56) References Cited

U.S. PATENT DOCUMENTS

2006/0015104 A1    1/2006  Dalton
2006/0155275 A1*   7/2006  Dongar et al. .................. 606/59
(Continued)

FOREIGN PATENT DOCUMENTS

FR        2 905 589        3/2008

OTHER PUBLICATIONS

International Search Report and Written Opinion dated Aug. 14, 2012 issued in International patent application No. PCT/FR2012/051125.

*Primary Examiner* — David Bates
*Assistant Examiner* — Olivia C Chang
(74) *Attorney, Agent, or Firm* — Ostrolenk Faber LLP

(57) ABSTRACT

The present disclosure relates to an osteosynthesis device comprising, on the one hand, a plate (12), which can be adjusted along a bone element (10), and at least one pin (26), and, on the other hand, a locking bushing (30) for rigidly connecting said plate (12) and said at least one pin (26). Said locking bushing (30) has a screwable part (32) and a drive part (34) separated from each other by a breakable zone (38), said screwable part having axial slits (44) that form notches (50). Said breakable zone (38) is intended to be broken in order to free said screwable zone (32) from said drive part (34). Said axial slits (44) extend into said breakable zone (38) so as to be able to fragment said screwable part (32) into independent notches (50) when said breakable zone (38) is broken, in order to be able to adjust the relative position of said notches (50) around said at least one pin (26).

10 Claims, 1 Drawing Sheet

(56) References Cited

U.S. PATENT DOCUMENTS

| | | |
|---|---|---|
| 2006/0195104 A1 | 8/2006 | Schlafli et al. |
| 2011/0060370 A1* | 3/2011 | Worcel ............... A61B 17/8047 606/281 |
| 2011/0060371 A1* | 3/2011 | Worcel .......................... 606/286 |

* cited by examiner

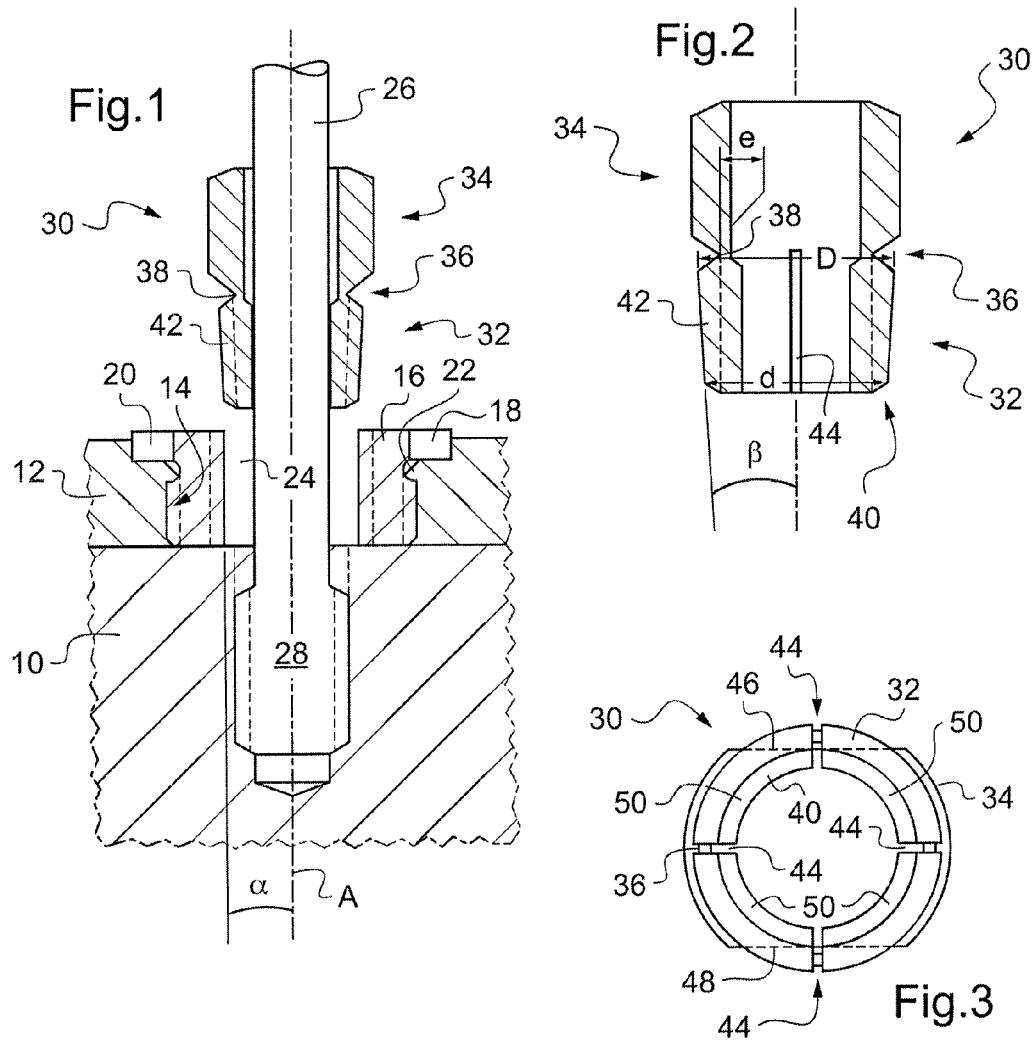
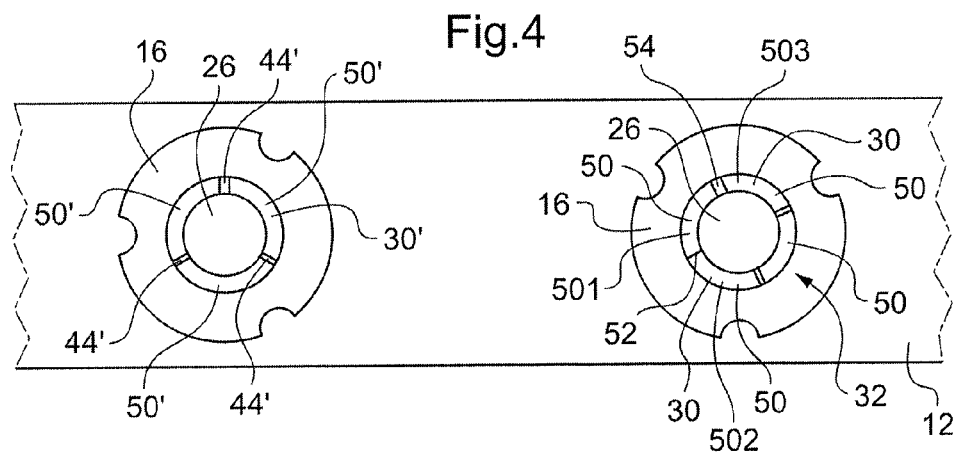

OSTEOSYNTHESIS DEVICE WITH PLATE AND PINS

CROSS REFERENCE TO RELATED APPLICATIONS

The present application is a 35 U.S.C. §371 National Phase conversion of PCT/FR2012/051125, filed May 21, 2012, which claims benefit of French Application No. 1154878, filed Jun. 6, 2011, the disclosure of which is incorporated herein by reference. The PCT International Application was published in the French language.

TECHNICAL FIELD OF THE INVENTION

The present invention relates to an osteosynthesis device for holding at least two bone elements in place relative to each other.

BACKGROUND OF THE INVENTION

Known devices comprise plates, and pins which are intended to be held in place through said plates by means of a locking bushing. The plates extend longitudinally in order to be able to be adjusted along the bone elements situated in the continuation of each other, and they have at least two tapped orifices which are respectively situated opposite the two bone elements. The tapped orifices obviously extend all the way through the plates.

As regards the locking bushings, they comprise a screwable part, and a drive part on top of the screwable part. Moreover, the two parts are separated from each other by a groove formed on the locking bushing. The screwable part has a free edge, and it has the general shape of a frustum, its diameter decreasing from the aforementioned groove toward the free edge. In addition, it has axial slits thus defining notches. During assembly, the plate is adjusted along the bone elements, whereas the pins are respectively anchored in these bone elements through the tapped orifices. After the anchoring, the pins have a residual free part which protrudes from the plate and on which the locking bushings will be engaged. The internal diameter of these bushings corresponds, allowing for functional clearance, to the external diameter of the pins, which makes it possible to guide them in translation. The screwable part is then brought to the area of the tapped orifice, and the bushing is engaged in rotation by means of the drive part arranged on top of it. When the screwable part engages with the threads of the tapped orifice, account being taken of its general frustoconical shape, the notches defined by the slits tend to deform concentrically, thus forming jaws which progressively clamp the pin. At a final stage of the driving in rotation of the screwable part, the pin remains in a fixed position with respect to the plate, the screwable part of the bushing being engaged with force between the walls of the tapped orifice of the plate and the pin. Obviously, such a procedure is undertaken for both pins, so as to hold the two bone elements in a fixed position relative to each other.

Thereafter, using cutting pliers engaged at right angles to the aforementioned groove, the bushing and the protruding pin part are both shorn off. In this way, the face of the plate opposite the bone elements is freed of the protruding elements, that is to say the drive part of the bushing and the free part of the pin, whereas the pin part anchored in the bone elements is rigidly connected to the plate by virtue of the locking bushing that clamps it.

Reference may be made to the document FR 2 905 589, which describes an osteosynthesis device of this kind.

These devices are presently in use and, although they permit rapid intervention and a good hold of the bone elements for a period of time sufficient for their consolidation, as compared to the previous generations of osteosynthesis devices, there is still a need for devices that are more effective and less expensive to use.

Thus, a problem which arises, and which is addressed by the present invention, is to make available a device that is more economical, easier to use and provides a high degree of reliability after it has been fitted.

SUMMARY OF THE INVENTION

To this end, the present invention proposes an osteosynthesis device comprising, on the one hand, a plate, which can be adjusted along a bone element, and at least one pin, which is intended to be anchored in said bone element through said plate, and, on the other hand, a locking bushing, which can receive said at least one pin and by means of which it is possible to rigidly connect said plate and said at least one pin, said locking bushing having a screwable part and a drive part for screwing said screwable part through said plate, said screwable part and said drive part being separated axially from each other by a breakable zone, said screwable part having axial slits that form notches between said axial slits, said screwable part being able to cooperate with said plate when said screwable part is screwed through said plate in order to be able to concentrically deform said notches and to clamp said pin, said breakable zone being intended to be broken in order to free said screwable part from said drive part. According to the invention, said axial slits extend into said breakable zone so as to be able to fragment said screwable part into independent notches when said breakable zone is broken, in order to be able to adjust the relative position of said notches around said at least one pin. A breakable zone is in fact a mechanically weaker zone which in this case extends between said screwable part and said drive part and in which the break takes place.

Thus, one feature of the invention lies in the locking bushing and more particularly in the provision of axial slits which extend into the breakable zone. In this way, when the breakable zone is broken, the notches of the screwable part forming jaws become independent of each other, and the radial tensions exerted between the pin and the plate tend to balance out in all the directions substantially parallel to the mean plane of the plate. Although independent, the jaws, which given the nature of the screwable part have thread portions engaged in the plate, are maintained axially in a fixed position with respect to the pin and the plate.

In addition, with the jaws becoming independent, and no longer rigidly connected to each other, the clamping of the pin is less sensitive to the hardness of the metals and to the clamping torque and to the precision of the machining of the components.

Moreover, as will be explained in more detail later in the description, although the fragmentation of the screwable part of the intermediate bushing permits better initial clamping, and therefore a more rigid assembly at the time of installation, this assembly changes over time and its rigidity decreases. Such a feature makes it possible to stress the bone elements progressively and mechanically and therefore to promote consolidation of bone.

According to one feature of a particularly advantageous embodiment of the invention, said breakable zone is self-breakable so as to be able to break said breakable zone when said notches clamp said at least one pin, while the drive part is driven with force. Thus, by virtue of this feature, there is no need to shear off the bushing, simply the pin, and, what is more, level with the screwable part, as will be explained in the description below. Moreover, when the drive part is driven with force and the jaws clamp the pin, the resistance of the screwable part in rotation becomes greater than the mechanical resistance of the breakable zone, which tends to deform by shearing in directions substantially parallel to the tangents to the bushing. Thus, the resistance in rotation of each of the notches of the screwable part is different according to the relative position of the pin and of the plate, and in particular their inclination, such that the deformation by shearing of the breakable zone takes place differently at right angles to the notches. In this way, and by virtue of the axial slits, the notches move closer to each other or away from each other circumferentially as the rupture progresses, depending on the resistance of each during their rotation. By virtue of this relative adjustment of the notches with respect to each other, the radial forces between the plate and the pin balance out perfectly. The notches then form independent wedges between the pin and the plate and they are held captive by the assembly. This is because, on the one hand, the threads of the notch are in engagement in the plate, and, on the other hand, the pin is bearing with force. Thus, the pin is perfectly maintained in a fixed position with respect to the plate.

Preferably, said locking bushing has a groove between said screwable part and said drive part in order to form said breakable zone. This groove is easily formed on the outside of the bushing, and its depth is precisely determined in order to calibrate the thickness of the bushing at the groove bottom. Indeed, this thickness must be predetermined as a function of the material, since it has to be sufficiently strong in order to drive the screwable part through the plate, but also has to break when the clamping of the notches, or jaws, is sufficient to lock the pin. The locking bushing is made, for example, of medical-grade stainless steel.

In addition, said screwable part has a free circular edge situated opposite said breakable zone, and the diameter of said screwable part advantageously decreases from said breakable zone toward said circular free edge. In this way, said screwable part cooperates with said plate, and more precisely with the tapped orifice of which the envelope is cylindrical for example, when said screwable part is screwed through said plate in order to be able to deform said notches concentrically. To do this, the maximum diameter of the screwable part must be greater than the diameter of the tapped orifice, as will be explained in more detail later in the description. Thus, during the rotation of the screwable part through the plate, the notches forming wedges are driven progressively between the plate and the pin and clamp it.

According to a particularly advantageous embodiment, said screwable part has a frustoconical envelope. Such a shape has the merit of being able to be easily produced. Moreover, the clamping of the pin is progressive as the screwable part is driven in rotation. According to another embodiment, provision is also made for a tapped orifice of the plate of frustoconical shape.

Furthermore, according to another particularly advantageous embodiment, the device additionally comprises an intermediate bushing intended to be screwed into the thickness of said plate, said locking bushing being intended to be engaged inside said intermediate bushing. Such an intermediate bushing, also called reducer, permits better adjustment and better centering of the pin. Moreover, the plate has tapped circular recesses through which the intermediate bushings engage. These intermediate bushings also have an internal thread forming the aforementioned tapped orifice. The intermediate bushing can then be mounted in place. Furthermore, the intermediate bushing permits disassembly of the osteosynthesis device after it has been installed. Indeed, the pin is totally rigidly connected to the intermediate bushing by virtue of the use of the locking bushing after installation in the bone element. Thus, after several weeks, in order to remove the device, the intermediate bushing is unscrewed with the pin, which is integrally connected thereto.

According to a preferred embodiment, said screwable part has four axial slits, diametrically opposite each other in pairs. Thus, upon assembly, four notches are obtained, or truncated segments, clamping the pin, which makes it possible to lock the latter radially in all directions. It is obviously also locked axially in view of the radial and concentric forces exerted on it.

In addition, said drive part of said locking bushing has two diametrically opposite flats which, by means of a simple wrench, allow the drive part to be driven in rotation. Of course, other shapes of the drive part are envisioned, in particular hexagonal shapes.

BRIEF DESCRIPTION OF THE DRAWINGS

Other features and advantages of the invention will become clear from reading the following description of a particular embodiment of the invention, given as a non-limiting example, and by referring to the attached drawings, in which:

FIG. 1 is a schematic view, in axial cross section, of an osteosynthesis device according to the invention in the process of assembly;

FIG. 2 is a schematic elevation of an element of the osteosynthesis device shown in FIG. 1;

FIG. 3 is a schematic bottom view of the element shown in FIG. 2; and

FIG. 4 is a schematic top view of elements of the osteosynthesis device shown in FIG. 1.

DESCRIPTION OF PREFERRED EMBODIMENTS

FIG. 1 partially illustrates a bone element 10 on which a plate 12 is applied. The latter has a circular recess 14, which is tapped and extends all the way through the plate along an axis of symmetry A. An intermediate bushing 16 is then fitted by being screwed inside the circular recess 14. The intermediate bushing 16 has a flange 18 in which radial indents 20 are formed for driving in rotation. Moreover, the plate 12 has a rebate 22 in which the flange 18 can be lodged at least in part. The intermediate bushing 16 has a tapped orifice 24. It will be noted that the tapped orifice 24 shown in FIG. 1 is of cylindrical symmetry. The intermediate bushing 16 is thus able to be rigidly connected to the plate 12 within the thickness thereof. According to a particularly advantageous embodiment of the invention, the tapped orifice 24 has a conical symmetry of revolution. The generatrix of the tapped orifice 24 and its axis of symmetry form an angle $\alpha$ of between 3° and 7°, for example.

This figure also illustrates a pin 26 which passes through the plate 12 and the tapped orifice 24 and is screwed inside the bone element 10. To do this, the pin 26 has a self-drilling end 28 which has been screwed into the bone element by way of the plate 12 and through a given thickness of the bone element depending on the possibilities and requirements of anchoring.

Moreover, the body of the pin 26 is engaged inside a locking bushing 30, which has a screwable part 32, oriented toward the intermediate bushing 16, and an opposite drive part 34. It will be noted from FIG. 1 that all the elements are arranged coaxially in relation to the circular recess 14.

The locking bushing 30, shown from the side in FIG. 2, will now be explained in detail. It is made of surgical steel, for example 316 L steel, which may or may not be strain-hardened. Its drive part 34 will be seen sitting on top of its screwable part 32. These two parts are separated from each other in an axial direction by a V-shaped groove 36 that forms a breakable zone. This groove 36 has a groove bottom 38, at right angles to which the thickness e of the bushing is on average between 0.5 and 3 mm, for example 1.5 mm. The groove bottom can also be provided with a thickness e that varies about the circumference. For example, thickened reinforcement areas, judiciously arranged, as will be explained below.

The screwable part 32 has a free lower edge 40, and its maximum diameter D, near the groove 36, is greater than its minimal diameter d, near the lower edge 40. Thus, the screwable part 32 has the general shape of a frustum of revolution, its diameter decreasing progressively from the groove 36 toward the free lower edge 40. The generatrix of the screwable part 32 and its axis of symmetry here form an angle β, advantageously greater than the angle α of the tapped orifice 24, for example of between 3° and 8°. The screwable part 32 also has an external thread 42. The advantages of the difference in cone angle between the screwable part 32 and the tapped orifice 24 will be explained in more detail later in the description.

In addition, and according to a particularly advantageous feature of the invention, the screwable part 32 of the locking bushing 30 has axial slits 44 which extend axially from the lower edge 40 to the groove 36 into which they open. Only one of these axial slits 44 appears in FIG. 2. They are spaced apart from one another, for example by 90°.

Reference is now made to FIG. 3, in which the locking bushing 30 is shown in more detail in a bottom view. This figure shows the screwable part 32 and its lower edge 40, and also the axial slits 44 opening into the groove 36. These axial slits 44 obviously extend along the axis of the bushing 30, but also radially within the thickness of the screwable part 32. The width of these axial slits 44 is close to the radial thickness of the screwable part 32 of the bushing, for example 0.7 times this thickness. The axial slits 44 as such define deformable notches 50, which are in the shape of truncated cone segments and are able to form jaws when they are deformed concentrically. It will be noted here that the reinforcement thicknesses at the groove bottom can be formed at right angles to the deformable notches, in such a way as to locally strengthen their connection to the drive part 34.

Extending to the rear of the screwable part 32 is the drive part 34, which has two diametrically opposite flats 46, 48 indicated by broken lines. These flats 46, 48 are intended to receive a simple spanner, for example an open-ended spanner or a suitable ring spanner, so as to be able to drive the screwable part 32 in rotation, as will be explained below.

We firstly refer once again to FIG. 1 to describe how the osteosynthesis device according to the invention is assembled, and then to FIG. 4 to describe the device after assembly and in two alternative embodiments.

Firstly, the groove 36, which separates the screwable part 32 from the drive part 34, and the external thread 42 are seen once again on the locking bushing 30 shown in FIG. 1. Proceeding from the position of the locking bushing 30 as shown in FIG. 1, the bushing is driven in a sliding movement, guided by the pin 26, as far as the intermediate bushing 16, and it will be driven in rotation by way of the drive part 34. The screwable part 32 then engages in the thread of the tapped orifice 24. In a first phase of screwing, the external thread 42 of the screwable part 32 and the thread of the tapped orifice 24 penetrate only slightly into each other, by virtue of the difference in angle of the screwable part 32 and of the tapped orifice 24. Indeed, when the screwable part 32 is fitted inside the tapped orifice 24, their threads engage each other along a shorter length than would be the case if they had the same conicity. As a result, in this first phase of screwing, the screwable part 32 does not deform and the pin 26 remains free with respect to the locking bushing 30. In this way, it can still be adjusted if necessary. Furthermore, the locking bushing 30 can still be unscrewed in order to readjust the pin 26.

Gradually, as the screwable part 32 engages inside the intermediate bushing 16, the external thread 42 and the thread of the tapped orifice 24 penetrate progressively into in each other, and frictional forces arise. This is due to the frustoconical shape of the screwable part 32 and of the tapped orifice 24. Thus, in a second phase of screwing, the rotation of the locking bushing 30 causes the concentric movements of the notches 50, which come to bear radially against the body of the pin 26. The notches 50, in the shape of truncated cone segments, form jaws or wedges that gradually wedge the body of the pin 26 and the intermediate bushing 16 while the locking bushing 30 is driven in rotation. The radial and concentric movements of the notches 50, and their swinging movement with respect to the drive part 34, are made possible by virtue of the axial slits 44 and also by virtue of their flexibility.

The frustoconical shape of the screwable part 32, with its maximum diameter D and minimum diameter d, is predefined with the geometric parameters of the frustoconical tapped orifice 24 and the diameter of the pin 26, in such a way that the screwable part 32 is situated in a position of relative locking when it is accommodated inside the intermediate bushing 16.

In this situation, therefore, a third phase of screwing begins in which the locking bushing 30 will deform by shearing at the groove bottom 38.

It will be readily appreciated that the pin 26 is not necessarily exactly perpendicular to the plate 12, nor is it perfectly cylindrical like the bushings 16, 30. Thus, in the third phase of screwing, the notches 50, still rigidly connected to one another, are driven with friction both against the inside of the tapped orifice 24 and also against the outside of the body of the pin 26. They are each therefore subjected to different frictional forces. Consequently, by virtue of the axial slits 44 which continue into the groove 36, the locking bushing 30, at right angles to its groove bottom 38 and to the notches 50, will deform differentially by shearing, depending on the frictional forces to which the notches 50 are precisely subjected. Thus, of the notches 50, the one that will be exposed to the greatest frictional force will cause a greater deformation of the opposite groove bottom 38 and, consequently, an initial shearing, while the other notches 50 remain driven in rotation until they in turn are exposed to substantial frictional forces. In this way, the shearing of the locking bushing 30 in the area of the groove bottom 38 is produced successively in the area of the notches 50 as they offer more and more resistance to the rotation movements. This makes it possible to drive the notches 50 successively into positions in which the radial stresses are substantially equivalent, before the drive part 34 is completely disconnected from the screwable part 32. In this way, the radial stresses which are applied to the body of the pin 26, and conversely inside the tapped orifice 24, are distributed uniformly about the pin 26. As a result, the latter is perfectly rigidly connected to the plate 12.

It will be noted that the thickness e of the bushing at the groove bottom 38 must, on the one hand, be sufficient to ensure that the locking bushing 30 can be screwed to the end of its travel in the intermediate bushing 16 without breaking, and, on the other hand, be sufficiently small to ensure that the locking bushing 30 can break precisely at the end of its travel. This position is reached when the screwable part 32 is lodged entirely in the thickness of the intermediate bushing 16 and, more precisely, when the groove 36 is situated at the upper part of the intermediate bushing 16.

In a system where the screwable part is in one piece, only the frictional forces due to the axial pressure between the screw threads oppose unscrewing. Here, by contrast, each notch 50 individually opposes unscrewing since, on the one hand, they have sharply defined edges that are able to anchor themselves in the walls of the pin and conversely in the walls of the intermediate bushing 16, and, on the other hand, they form a wedge between the pin 26 and the intermediate bushing 16. Their anchoring is all the stronger the greater the clamping torque has been. In addition, the notches 50, by forming a wedge, act on the entire length of the thread of the intermediate bushing 16, whereas, according to the prior art, the clamping was localized axially and acted only around the deformable part of the locking bushing. Thus, a perfectly rigid assembly of intermediate bushing 16 and pin 26 is obtained which will nevertheless evolve and deform over time and benefit the consolidation of the bone, as will be explained below.

Indeed, the notches 50, wedged between the pin 26 and the intermediate bushing 16, will be stressed and subjected to forces that are exerted on the bone element 10 and, consequently, on the plate 12 and the pin 26. Thus, over the course of time, that is to say after several weeks, the notches 50 will deform, for example by strain-hardening, and will also become worn by friction. Consequently, the connection between the pin 26 and the intermediate bushing 16, and therefore the plate 12, will become less and less rigid while they still remain integral with each other. Thus, at the outset, the assembly composed of the pin 26 and of the intermediate bushing 16 is very rigid, thereby allowing very rapid recovery of the functions of the limbs which it consolidates, with reduced post-operative pain. Subsequently, as time passes, it is able to deform more easily, which permits a gradual transfer of the mechanical stresses to the bone elements, which benefits their consolidation. In this way, the osteosynthesis device according to the invention is able to evolve mechanically toward less rigidity and thus makes it possible to gradually dynamize the ossification.

After the drive part 34 has been freed from the screwable part 32, cutting pliers will be used to shear the pin 26 precisely level with the screwable part 32 and the intermediate bushing 16.

Thus, a screw is obtained of which the shank, formed by a pin portion, and the head, formed by the intermediate bushing 16 and the screwable part 32 of the locking bushing 30, are rigidly joined in situ. In this way, the useful length of the shank is adapted depending on the depth of screwing of the pin inside the bone element, and on the relative position of the plate 12 and of the intermediate bushing 16.

It will be noted that the center of pivoting of the pin 26 with respect to the intermediate bushing 16 is situated at the shorn-off end of the pin 26, the notches 50 remaining intact, whereas the pin 26 tends to be driven in swinging movements at the side toward the bone element 10. It is therefore at this side of the bone element 10 that the notches 50 tend to strain-harden.

In addition, the plate 12 and the pin 26 are totally isolated from each other and are held in place relative to each other by way of the notches 50, which take up the escape of the stresses. For example, if one pin has a greater support in a cortical part compared to the other pins screwed into the spongy parts, the notches 50 will firstly take up the differences in stresses. This will make it possible to equilibrate the stresses in the device.

We now refer to FIG. 4 showing, in a top view, the plate 12 with two pins 26 spaced apart from each other and held in place inside an intermediate bushing 16 by means of a locking bushing 30 as illustrated in FIGS. 2 and 3, for one of the pins, and another locking bushing 30' in an alternative embodiment for the other of the pins. This other locking bushing 30' no longer has four axial slits, simply three axial slits 44'.

First of all, the locking bushing 30 as described above will be seen, more specifically the four notches 50 formed by its screwable part 32. Indeed, during the third phase of screwing, the rotation of the notches 50 has taken place by different amplitudes depending on the friction. Thus, among the notches 50, some 501, 502 have come into contact with each other in the area of a contact joint 52, causing the space of the slit 44 that separated them to disappear, whereas some others 501, 503 are spaced apart from each other, enlarging the space 54 of the slit 44 that separated them.

As regards the other locking bushing 30' for which only three slits 44' have been formed, it will be noted in the same way that the spaces defined by the slits have been made smaller or else enlarged during the third phase of screwing.

Moreover, according to one embodiment of the invention not shown here, four axial slits are formed in the screwable part of the locking bushing, but only two of them, diametrically opposite each other, open into the breakable zone. Thus, the notches are divided into two pairs of related notches. In this way, the two related notches are deformable relative to each other, while the two pairs of notches are independent of each other about the pin. Such a configuration affords other possibilities of fitting.

What is claimed is:

1. An osteosynthesis device comprising, a plate, which can be adjusted along a bone element, at least one pin, which is configured to be anchored in said bone element through said plate, and a locking bushing configured to receive said at least one pin and configured to rigidly connect said plate and said at least one pin, said locking bushing having a screwable part and having a drive part operable for screwing said screwable part through said plate, a breakable zone axially separating said screwable part and said drive part, said screwable part having axial slits that form wedges spaced by said axial slits, said screwable part being configured to cooperate with said plate when said screwable part is screwed through said plate to concentrically deform said wedges and to clamp said at least one pin, said breakable zone being breakable to free said screwable part from said drive part;
wherein said axial slits extend into said breakable zone to fragment said screwable part into independent wedges when said breakable zone is broken, for enabling adjusting the relative positions of said wedges around said at least one pin.

2. The osteosynthesis device as claimed in claim 1, wherein said breakable zone is self-breakable to break said breakable zone when said wedges clamp said at least one pin, while said drive part is driven with force.

3. The osteosynthesis device as claimed in claim 1, wherein said locking bushing has a groove between said screwable part and said drive part to define said breakable zone and said axial slits extend into said groove.

4. The osteosynthesis device as claimed in claim 1, wherein said screwable part has a free circular edge situated opposite said breakable zone, and an external diameter of said screwable part decreases from said breakable zone toward said free circular edge.

5. The osteosynthesis device as claimed in claim 4, wherein said screwable part has a frustoconical envelope of revolution, said screwable part having a generatrix that forms an angle β with an axis of symmetry of said screwable part.

6. The osteosynthesis device as claimed in claim 1, further comprising an intermediate bushing configured to be screwed into an opening in said plate, said locking bushing being configured to be engaged inside said intermediate bushing.

7. The osteosynthesis device as claimed in claim 6, wherein said intermediate bushing has a tapped orifice of frustoconical symmetry of revolution, said tapped orifice having a generatrix that forms an angle α with an axis of symmetry of said intermediate bushing.

8. The osteosynthesis device as claimed in claim 5, further comprising an intermediate bushing configured to be screwed into an opening in said plate,
   wherein said intermediate bushing has a tapped orifice of frustoconical symmetry of revolution, said tapped orifice having a generatrix that forms an angle α with an axis of symmetry of said intermediate bushing; and
   wherein the angle β of said screwable part is greater than the angle α of said tapped orifice.

9. The osteosynthesis device as claimed in claim 1, wherein said screwable part has four axial slits, diametrically opposite each other in pairs.

10. The osteosynthesis device as claimed in claim 1, wherein said drive part of said locking bushing has two diametrically opposite flats.

* * * * *